(12) United States Patent
Rao et al.

(10) Patent No.: US 10,365,266 B2
(45) Date of Patent: Jul. 30, 2019

(54) MOLECULAR CHARACTERIZATION OF CIRCULATING TUMOR CELLS

(71) Applicant: Menarini Silicon Biosystems, Inc., San Diego, CA (US)

(72) Inventors: Galla Chandra Rao, Princeton Junction, NJ (US); Brad Foulk, Chalfont, PA (US); Denis Smirnov, Media, PA (US); Karl Nielsen, Pitman, NJ (US)

(73) Assignee: Menarini Silicon Biosystems, Inc., San Diego, CA (US)

( * ) Notice: Subject to any disclaimer, the term of this patent is extended or adjusted under 35 U.S.C. 154(b) by 0 days.

(21) Appl. No.: 15/729,957

(22) Filed: Oct. 11, 2017

(65) Prior Publication Data

US 2018/0045712 A1 Feb. 15, 2018

Related U.S. Application Data

(62) Division of application No. 14/211,630, filed on Mar. 14, 2014, now Pat. No. 9,823,238.

(Continued)

(51) Int. Cl.
*G01N 33/50* (2006.01)
*G01N 33/58* (2006.01)
(Continued)

(52) U.S. Cl.
CPC ..... *G01N 33/5005* (2013.01); *G01N 33/5044* (2013.01); *G01N 33/54313* (2013.01);
(Continued)

(58) Field of Classification Search
CPC .......... G01N 33/5005; G01N 33/5044; G01N 33/54313; G01N 33/5436;
(Continued)

(56) References Cited

U.S. PATENT DOCUMENTS

| 6,365,362 B1 | 4/2002 | Terstappen et al. |
| 7,364,921 B1 | 4/2008 | Sciorra et al. |

(Continued)

FOREIGN PATENT DOCUMENTS

| CN | 18871517 A | 11/2006 |
| CN | 101469310 A | 7/2009 |

(Continued)

OTHER PUBLICATIONS

Peeters et al. Semiautomated isolation and molecular characterization of single or highly purified tumour cells from CellSearch enriched blood samples using dielectrophoretic cell sorting. British Journal of Cancer 105: 1358-1367 (Mar. 7, 2013).*

(Continued)

*Primary Examiner* — Gailene Gabel
(74) *Attorney, Agent, or Firm* — Foley & Lardner LLP (57) ABSTRACT

The disclosed invention includes methods and kits for the removal of white blood cells from samples of immunomagnetically enriched rare cells by treating the sample with a leukocyte marker conjugated to a hapten which adheres to the white blood cells and treating the resulting product with a second medium that adheres to the hapten of the white blood cells that are labeled with the leukocyte marker conjugated to hapten and removing the labeled white blood cells.

18 Claims, 7 Drawing Sheets

Depiction of hapten based white blood cell removal

Related U.S. Application Data (60) Provisional application No. 61/787,611, filed on Mar. 15, 2013.

(51) Int. Cl.
  *G01N 33/543* (2006.01)
  *G01N 33/574* (2006.01)
  *G01N 33/68* (2006.01)

(52) U.S. Cl.
  CPC . *G01N 33/54326* (2013.01); *G01N 33/54333* (2013.01); *G01N 33/57492* (2013.01); *G01N 33/582* (2013.01); *G01N 33/583* (2013.01); *G01N 33/585* (2013.01); *G01N 33/6854* (2013.01)

(58) Field of Classification Search
  CPC ....... G01N 33/54333; G01N 33/57492; G01N 33/582; G01N 33/583; G01N 33/585; G01N 33/6854
  See application file for complete search history.

(56) References Cited

U.S. PATENT DOCUMENTS

| | | | |
|---|---|---|---|
| 7,901,950 B2 | 3/2011 | Connelly et al. | |
| 8,889,361 B2* | 11/2014 | Chen | C12Q 1/6886 435/6.14 |
| 9,034,658 B2 | 5/2015 | Barber et al. | |
| 2002/0177176 A1* | 11/2002 | Thomas | C07K 16/28 435/7.21 |
| 2009/0136946 A1 | 5/2009 | Connelly et al. | |
| 2009/0191535 A1* | 7/2009 | Connelly | G01N 33/574 435/2 |
| 2010/0111916 A1* | 5/2010 | Xiang | A61K 35/15 424/93.71 |
| 2013/0129771 A1* | 5/2013 | Yarkoni | A61K 35/16 424/193.1 |
| 2013/0189675 A1 | 7/2013 | Gross et al. | |
| 2014/0011685 A1 | 1/2014 | Wang et al. | |
| 2015/0050298 A1* | 2/2015 | Fletcher | A61K 35/26 424/184.1 |

FOREIGN PATENT DOCUMENTS

| | | |
|---|---|---|
| CN | 102036753 A | 4/2011 |
| WO | WO 91/07660 A1 | 5/1991 |
| WO | WO 01/14591 A1 | 3/2001 |
| WO | WO 2011/063416 A | 5/2011 |

OTHER PUBLICATIONS

Chen-Lin Chen et al. (Separation and detection of rare cells in a microfluidic disk via negative selection. Lab on Chip 11: 474-483 (2011).*

Bilkenroth et al., "Detection and enrichment of disseminated renal carcinoma cells from peripheral blood by imnunomagnetic cell separation", International Journal of Cancer, vol. 92 , No. 4, May 15, 2001 (May 15, 2001), pp. 577-582 , XP055127483, ISSN: 0020-7136, DOI: 10.1002/ijc.1217 the whole document.

Bingxiu et al., "Comparison of three immunomagnetic bead methods for enriching circulating blood tumor cells", a Collection of Abstracts of Paper from 2003 Academic Exchanges of the Society of Biochemistry and Molecular Biology of the Six Provinces and One City in East China, p. 21, Aug. 2003.

Chen et al., "Separation and detection of rare cells in a microfluidic disk via negative selection", Lab on a Chip, vol. 11, No. 3. Jan. 1, 2011 (Jan. 1, 2011), pp. 474-483, XP055127437, ISSN: 1473-0197, DOI: 10.1039/c0lc00332h p. 478, right-hand column, paragraph 2-paragraph 3; figure 1.

EP Communication dated Feb. 2, 2017, in EP 14721102.3.

Jatana et al., "Significance of Circulating Tumor Cells in Patients With Squamous Cell Carcinoma of the Head and Neck" Archives of Otolaryngology—Head and Neck Surgery, vol. 136, No. 12, Dec. 20, 2010 (Dec. 20, 2010), p. 1274, XP055127484, ISSN: 0886-4470, DOI: 10.1001/archoto .2010.223 the whole document.

Lara et al., "Comparison of Two Immunomagnetic Separation Technologies to Deplete T Cells From Human Blood Samples", Biotechnology and Bioengineering, vol. 94, No. 1, pp. 66-80, published online on Mar. 3, 2006.

Lara et al., "Enrichment of rare cancer cells through depletion of normal cells using density and flowthrough, inmunomagnetic cell separation", Experimental Hematology, Elsevier Inc, US, vol. 32, No. 10, Oct. 1, 2004 (Oct. 1, 2004). pp. 891-904, XP004613157, ISSN: 0301-472X, DOI:10 . 1016/J . EXPHEM.2004.07.007 the whole document.

Liu et al., "Negative enrichment by immunomagnetic nanobeads for unbiased characterization of circulating tumor cells from peripheral blood of cancer patients", Journal of Translational Medicine, Biomed Central, London, GB, vol. 9, No. 70, May 19, 2011 (May 19, 2011), XP021100797, ISSN: 1479-5876, DOI:10.1186/1479-5876-9-70 p. 2, right-hand column, paragraph 3-p. 3, left-hand column, paragraph 2.

Li-Yirong et al., "Isolation of eosinophilis from peripheral blood by the negative selection procedure of magnetic activated cell sorting" Chinese Journal of Immunology vol. 16, No. 8 pp. 423-427 Dec. 31, 2000 (US abstract only).

Miltenyis et al., "High Gradient Magnetic Cell Seperation With Macs", Cytometry, Alan Liss, New York, US, vol. 11, No. 11, Jan. 1, 1990 (Jan. 1, 1990), pp. 231-238, XP000999711, ISSN: 0196-4763, DOI:10.1002/CYT0.990110203 the whole document.

Partridge et al., " Imnunomagnetic separation for enrichment and sensitive detection of disseminated tumour cells in patients with head and neck SCC" , The Journal of Pathology, vol. 189, No. 3, Nov. 1, 1999 (Nov. 1, 1999), pp. 368-377, XP055127482, ISSN: 0022-3417, D01:10.1002/(SICI)1096-9896(199911)189:3<368::AID-PATH441>3 .0.C0;2-2 the whole document.

Peeters et al., "Semiautomated isolation and molecular characterisation of single or highly purified tumour cells from CellSearch enriched blood samples using dielectrophoretic cell sorting", British Journal of Cancer, vol. 108, No. 6, Mar. 7, 2013 (Mar. 7, 2013), pp. 1358-1367, XP055339897.

Riethdorf et al., "Detection of circulating tumor cells in peripheral blood of patients with metastatic breast cancer: a validation study of the CellSearch system", Clinical Cancer Research, The American Association for Cancer Research, US, vol. 13, No. 3, Feb. 1, 2007 (Feb. 1, 2007), pp. 920-928, XP002516029.

Stem Cell Technologies (CD45 Depletion Kit: Easy Sep Stem Cell Technologies)—product literature, Mar. 2013.

Yang et al., "Optimization of an enrichment process for circulating tumor cells from the blood of head and neck cancer patients through depletion of normal cells", Biotechnology and Bioengineering, vol. 102, No. 2, Feb. 1, 2009 (Feb. 1, 2009), pp. 521-534, XP055029603, ISSN:0006-3592, DOI:10.1002/bit.22066 p. 524, right-hand column, paragraph 2—p. 526, right-hand column, paragraph 3; figures 2,3; table II.

Zigeuner et al., "Immunomagnetic Cell Enrichment Detects More Disseminated Cancer Cells Than Immunocytochemistry in Vitro", Journal of Urology, Lippincott Williams & Wilkins, Baltimore, MD, US, vol. 164, No. 5, Nov. 1, 2000 (Nov. 1, 2000), pp. 1834-1837, XP005554031, ISSN: 0022-5347, DOI:10.1016/S0022-5347(05)67116-9 the whole document.

Office Action dated Jan. 25, 2018, in EP 14721102.3.

Anonymous, "Fluorescent Microspheres," Product Data Sheet 731, Bangs Laboratories, Inc., Oct. 1, 2009, 1-2, XP055442714.

Verbarg et al., "Spinning magnetic trap for automated microfluidic assay systems," Lab on a Chip, Jan. 1, 2012, 12(10):1793, XP055072588.

Office Action dated Mar. 20, 2018, in JP 2016-502523, with English translation.

* cited by examiner

Figure 1 Depiction of hapten based white blood cell removal

Figure 2 Analysis of white blood cells and SKBR3 tumor cells before and after incubation with anti-FITC plate by flow cytometry Figure 3 Percent Removal of white blood and tumor cells by anti-FITC coated plate Figure 4_Molecular measurement of WBC removal.

Figure 5. Improved detection of CTC markers following CD45 depletion

Figure 6. High correlation between spiked-in Vcap cells with WBC depletion v/s Vcap cultured cells. Gene expression of Androgen Receptor (AR), two AR splice variants (ARV1 and ARV3/7), TMPRSS2 and TMPRSS2:ERG splice variants from spiked-in Vcap cells with WBC depletion v/s Vcap cultured cells ranging from 100, 50, 25, and 10 was performed respectively. Taqman assay results were normalized using internal control RPL19 expression. The Pearson correlation and P-value are shown.

Figure 6

Figure 7 Effect of bead depletion on white blood cell and tumor cell markers

MOLECULAR CHARACTERIZATION OF CIRCULATING TUMOR CELLS

RELATED APPLICATIONS

This application is a divisional application of U.S. application Ser. No. 14/211,630, filed Mar. 14, 2014, issued as U.S. Pat. No. 9,823,238, which claims priority to U.S. Provisional Application Ser. No. 61/787,611, entitled "Improved Molecular Characterization of Circulating Tumor Cells" which was filed on Mar. 15, 2013.

BACKGROUND

Circulating tumor cells (CTC) of epithelial origin are present in the blood of carcinoma patients at very low frequency (<10/ml blood). The detection of tumor cells in circulation may have significance for cancer disease management. The detection of low frequency cells requires a large blood volume for processing. In order to enumerate and characterize CTCs from large blood volumes, the enrichment of CTCs is necessary.

Several methods are available to enrich CTCs based on size, density and antigen. The well established commercial product for enrichment of rare cells is Veridex CellSearch CTC assay. The CellSearch CTC assay uses magnetic particles conjugated to anti-epithelial cell adhesion molecule (EpCAM) to capture CTCs from 7.5 ml of blood. The enriched samples are stained with DAPI, a nucleic acid dye, to identify nucleated cells, anti-cytokeratin antibodies conjugated to phycoerythrin in order to identify cells of epithelial origin, and anti-leukocyte antibodies conjugated to allophycocyanin to identify all leukocytes. The samples are analyzed on a CellTracks Analyzer II for enumeration of CTCs.

The final sample after the enrichment contains CTCs and a small number of white blood cells (1000-5000 cells). The enrichment method removes more than 99% of white blood cells (WBC). The presence of white blood cells during the enumeration of rare cells is not an issue does not adversely affect the process. WBCs may be labeled with a leukocyte marker (CD45) to differentiate WBCs from CTCs. However, if one wants to molecularly characterize the enumerated CTCs to define their genotype by amplification of the nucleic acids present in such CTCs the presence of white blood cells in adversely affects this characterization. Given that the ratio of white cells in an enumerated fraction is high compared to the number of CTCs and the nucleic acids of such white cells is amplified with the CTCs it is difficult was difficult to determine the source of the nuclei acids, namely CTCs or white blood cells. As a result, further purification of enriched samples to remove white blood cells (decrease the ratio of white blood cells to CTCs) would be a major milestone for developing a reliable molecular characterization tools. This need is met by the following invention.

There are no methods available to remove white blood cells after the enrichment of CTCs. It requires a unique method since the same principle used for the enrichment of CTCs will not be used. For example, if the enrichment method in the first step uses the immunomagnetic method, another method besides the immunomagnetic method must be used.

DETAILED DESCRIPTION OF THE DRAWINGS

DETAILED DESCRIPTION OF INVENTION

An invention described herein comprises, consists essentially of or consists of a method of removing white blood cells from a sample comprising enriched rare cells and white blood cells such method comprises
  (a) treating such sample with a leukocyte marker that is conjugated to a hapten under conditions that label such white blood cells with such leukocyte marker conjugated to a hapten
  (b) treating the composition of step (a) with a second medium that adheres to such labeled white blood cells, and separating the second medium and its adhered labeled white blood cells from the composition of step (b).

As used herein "leukocyte markers" refer to substances that label white blood cells and not rare cells, Examples of leukocyte markers include but are not limited to antibodies to CD45, CD19, CD15, glycophorin A, CD2, CD14. CD16, CE38, and CD66b. The preferred leukocyte marker is anti CD45. Haptens include but are not limited to fluorescein dye ("FITC") phycoerythrin ("PE"), allophycocyanin ("APC") and biotin. The preferred hapten is FITC. As used herein the term antibodies includes whole antibodies both monoclonal and polyclonal, antibody fragments that bind with the certain haptens, bi-specific antibodies that bind to certain haptens. The preferred antibodies are monoclonal antibodies.

As used herein, "second medium" means any surface comprising a second marker, other than a leukocyte marker. Such second marker binds to the hapten that is conjugated to the leukocyte marker. Examples of second markers include but are not limited to antibodies to FITC, PE, APC, the preferred second markers are antibodies to FITC. An example of a surface that may be used is a microtiter plate.

As used herein "rare cells" are cells that have a low frequency in blood. Examples of rare cells include but are not limited to circulating tumor cells (CTCs), circulating endothelial cells (CECs) circulating multiple myeloma cells (CMMCs) and circulating melanoma cells (CMCs). The preferred rare cells are CTCs and CECs, the particularly preferred rare cells are CTCs. Enriched fractions of these rare cells may be produced from whole blood by known methods. Such methods include but are not limited to the methods and reagents disclosed in the following patents and patent applications: U.S. Pat. Nos. 7,901,950; 6,365,362, US Pat. Pub. Nos. US 2009/0136946; US 2013/0189675; US 2014/0011685 which are hereby incorporated by reference in their entirety. The preferred method of obtaining enriched CTCs is by the immunomagnetic methods disclosed in references such as U.S. Pat. No. 6,365,362 and by the methods of the CELLSEARCH product line.

Figure 1:
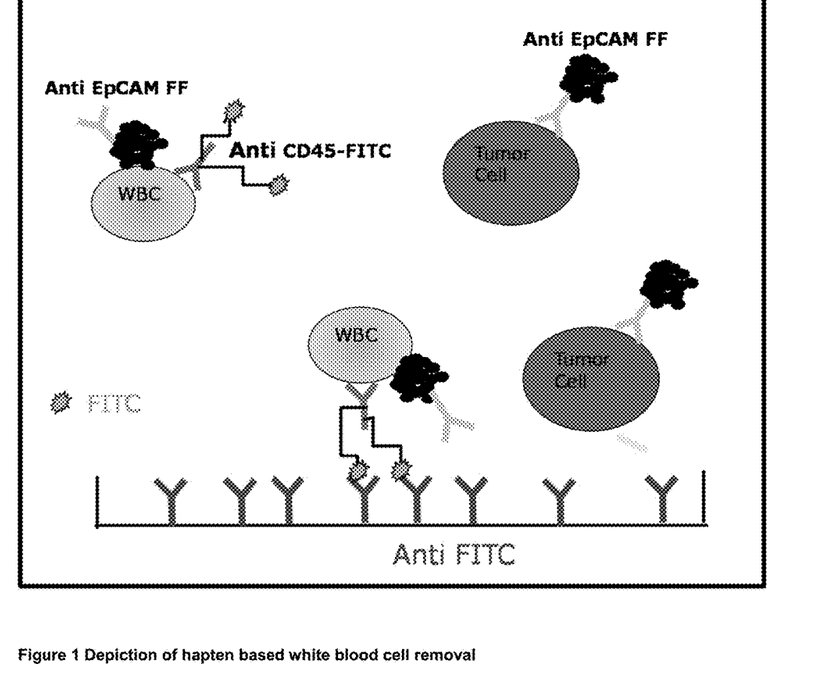
FIG. 1 Depiction of hapten based white blood cell removal

The principle of depleting white blood cells from an enriched fraction of CTCs. The CTCs and the white blood cells are labeled with an antiEpCAM ferrofluid and the white blood cell is labeled with a leukocyte conjugated hapten is illustrated in FIG. 1.

Further the invention includes a kit for removing white blood cells from a sample comprising enriched rare cells and white blood cells wherein such kit comprises a leukocyte marker that is conjugated to a hapten and a second marker, other than the leukocyte marker wherein the second marker comprises antibodies to such haptens.

All of the defined terms have the same definitions and preferred examples as described above.

Still further the invention includes a kit for removing white blood cells from a sample comprising enriched rare cells and white blood cells wherein such kit comprises reagents for immunomagnetically marking the rare cells and white blood cells, a leukocyte marker that is conjugated to a hapten and a second marker, other than the leukocyte marker wherein the second marker comprises antibodies to such haptens.

All of the defined terms have the same definitions and preferred examples as described above.

The invention is illustrated by the following examples, which are not meant to limit the invention's scope.

EXAMPLES

Example 1: Depletion of White Blood Cells Using Anti CD45 Coated on a Microtiter Plate This example shows the depletion of white blood cells using anti CD45. CD45 is a common leukocyte marker present on white blood cells and it is expected that all white blood bind to anti CD45. We used anti-CD45 to bind white blood cells and specifically remove them from a mixture of white blood cells and CTCs using a solid phase coated with anti CD45. Anti-CD45 was coated to a solid phase as follows:

Anti-CD45 (Veridex) was diluted to 50 ug/ml in 50 mM sodium bicarbonate buffer pH 8.5. 0.8 ml of anti-CD45 antibody solution was then added to 6 well microtiter plate, incubated for 3 hours at room temperature (RT) followed by overnight at 2-8° C. After overnight incubation, anti CD45 antibody was aspirated and the wells were blocked with 1 ml of PBS/1% BSA at RT for 4 hours. The buffer was aspirated and the wells were rinsed with 2 ml of PBS 2-times. After the rinse, the entire buffer was aspirated and the plate was dried for 1 hour. The plate was stored dry in a sealed plastic bag at 2-8° C. until use.

In this example, two experiments were done to test the principle of separating white blood cells from non-white blood cells. In one study, pure white blood cells were prepared from whole blood after lysing red blood cells using BD lysing reagent. This sample was used as a positive control. In another study, 7.5 ml of blood was processed on the CellTracks AutoPrep system using CellSearch CTC Profile kit. The CTC Profile kit contains anti-epithelial cell adhesion molecule (EpCAM) conjugated to ferrofluid magnetic particles for the capture of circulating tumor cells. After the enrichment of target cells, the samples were resuspended in 900 ul of PBS/1% BSA buffer. The enriched samples will contain target cells and also white blood cells. Before samples were added to the wells in the microtiter plate, the plate was brought to room temperature (minimum of 30 minutes), the wells were washed twice with 2 ml of PBS/5% BSA. The buffer from the wells was then aspirated before the sample was added. The 900 ul CTC assay sample and pure white blood cells from whole blood were added to two separate wells of the plate. Following a 1 hour incubation with gentle mixing every 15 minutes, 300 ul of supernatant was removed to determine the numbers of white blood cells. The number of white blood cells present in the sample was determined by FACSCalibur flow cytometer (Beckton Dickinson) using forward scatter as a threshold. If the white blood cells bind to anti-CD45 in the wells then the number of white blood cells in the supernatant should be decreased when compared to the sample before the incubation step. The unbound cells should be in the supernatant. The results are shown in Table 1a.

Table 1a.

TABLE 1a

White blood cell numbers before and after incubation with anti CD45 coated onto a microtiter plate

| | WBC # | | |
|---|---|---|---|
| Sample | Before incubation with anti-CD45 coated plate | After incubation with anti-CD45 coated plate | % WBC Removal |
| White blood cells without CTC assay | 1000 | 200 | 80 |
| CTC assay sample | 1200 | 1300 | 0 |

The above results show that pure white blood cells can be removed by adding them to the microtiter plate coated with anti-CD45. However, white blood cells were found in the supernatant of the CTC assay sample. This suggests that white blood cells from the CTC assay sample did not bind to anti-CD45 coated in the wells. The difference between the two samples is that white blood cells in the CTC assay sample are labeled with ferrofluid magnetic particles. It is possible that ferrofluid magnetic particles present on white blood cells are preventing binding to anti-CD45 on the plate due to steric hindrance. To overcome this problem, the samples from the CTC assay were first labeled with anti-CD45 conjugated to a hapten by a linker (See Examples). The samples containing white blood cells prelabeled with the anti-CD45-tag were then added to a microtiter plate coated with anti-hapten.

Example 2: Coating of Anti-Fluorescein Isothiocyanate (FITC) to the Microtiter Plate Anti-FITC was purchased from BD Biosciences and diluted to 50 ug/ml in 50 mM sodium bicarbonate, pH 8.5. 800 ul of anti-FITC was added to 6 well microtiter plates, incubated at RT for 3 hours followed by overnight at 2-8° C. After overnight incubation, the plate was brought to RT. The supernatant was aspirated and then the plate was rinsed twice with PBS. The wells were then blocked with 1 ml of PBS/1% BSA for 4 hours at RT. The buffer was aspirated and the wells were rinsed with 2 ml of PBS 2-times. After the rinse, the entire buffer was aspirated and the plate was dried for 1 hour. The plate was stored dry in a sealed plastic bag at 2-8° C. until use. The plate was brought to RT (minimum of 30 minutes) on the day of use. 2 ml of PBS/1% BSA was added to the wells and incubated for 15 minutes. Following aspiration the plate was once again rinsed with 2 ml of PBS/1% BSA. The buffer was aspirated before sample was added to the well.

Example 3: Removal of White Blood Cells from CTC Assay Sample where White Blood Cells are Labeled with Anti-CD45 Conjugated to FITC and Microtiter Plate Coated with Anti-FITC 7.5 ml of EDTA blood spiked with SKBR3 cells was processed on the AutoPrep using CellSearch CTC kit. This enriched sample from the CTC assay was stained with anti-CD45-FITC at a final concentration of 2 ug/ml. The excess CD45-FITC was removed by washing the sample 2-times with 2 ml of PBS/1% BSA by magnetic separation for 15 minutes. The final sample was resuspended in 900 ul of PBS/5% BSA and then applied to the wells coated with anti-FITC. The samples were incubated for 1 hour with gentle mixing every 15 minutes. After one hour, 300 ul of supernatant was removed from the wells and the number of white blood cells and SKBR3 cells were determined by flow cytometer. To detect SKBR3 cells by flow cytometry, the cells were labeled with anti-Her2neu conjugated to allophycocyanin dye (APC). The white blood cells were detected in the FITC channel since they were labeled with anti-CD45-FITC. The cells detected before and after depletions are shown in FIG. 2.

Figure 2:
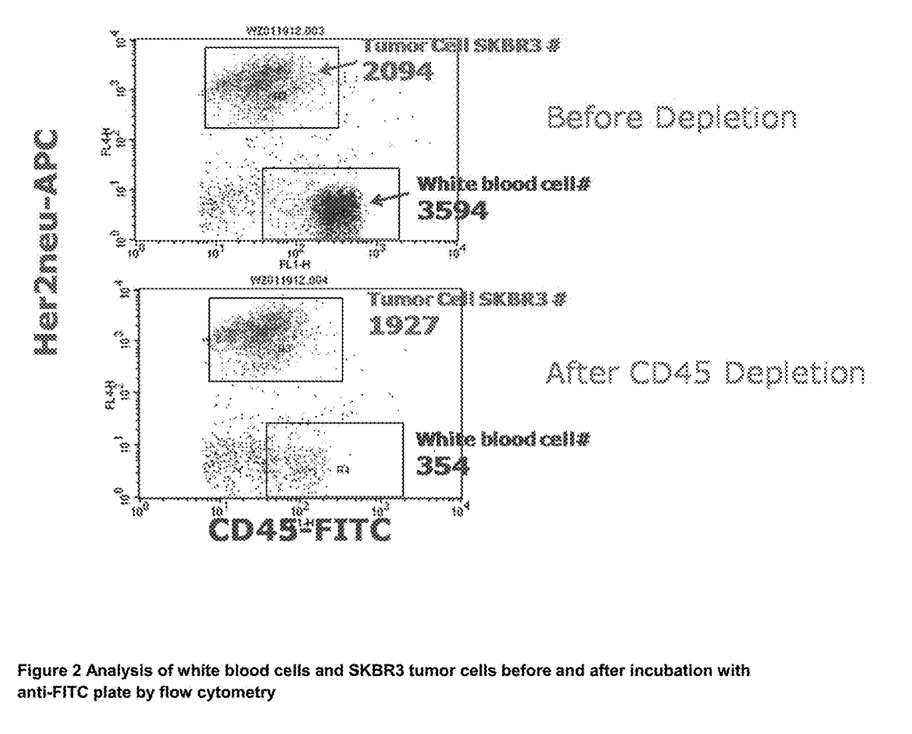
FIG. 2 Analysis of white blood cells before and after incubation with anti-FITC
Figure 3:
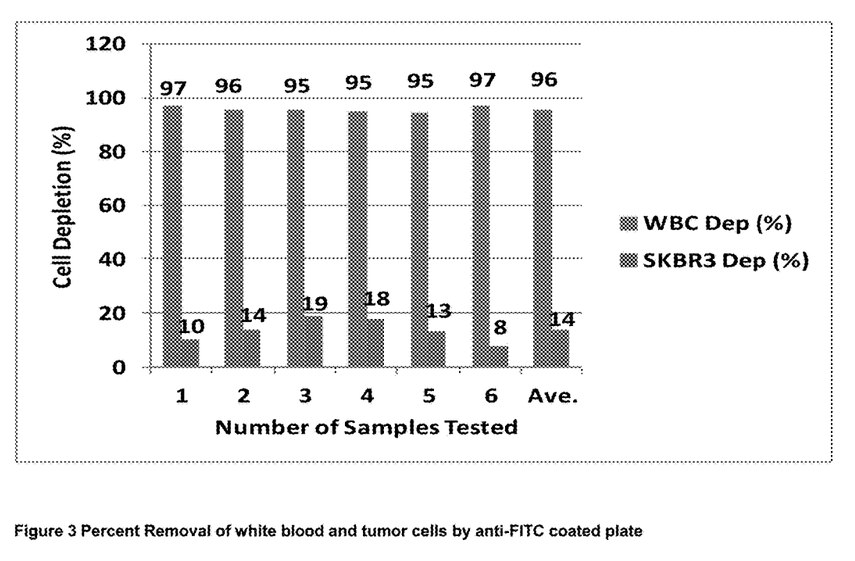
FIG. 3 Percentage white blood cell removal

FIG. 2 shows the number of tumor and white blood cells before and after depletion of white blood cells. The number of white blood cells before and after depletion are 3594 and 354, respectively which indicates that approximately 90% of white blood cells are depleted from the sample. On the other hand, the number of tumor cells before and after depletion are 2094 and 1924, respectively which indicates that all the tumor cells (>90%) are present in the supernatant. This example shows that white blood cells present in the CTC assay sample after tumor cell enrichment can be removed using the invention This was tested with on 6 samples and the results are shown in FIG. 3. The results show that more than 90% of WBCs can be removed with minimal loss (<15%) of tumor cells (SKBR3).

Example 4: Depletion of White Blood Cells in Circulating Endothelial Cell (CEC) Assay This example shows that the principle of WBC depletion can be applied to other rare cell assays. The CellSearch CEC assay enriches CECs from blood using CellSearch CEC kit. The kit contains anti-CD146 conjugated to ferrofluid magnetic particles for the capture of CECs. The assay uses CellTracks AutoPrep system for the sample preparation much like the CTC assay. While CECs are present at a low frequency in normal healthy blood samples, they are elevated by various conditions such as cancer, cardiovascular problems and infection.

The assay was used to test the effect of the depletion principle on CECs present at low a frequency (1-20 cells per test) in addition to WBCs depletion efficiency.

4 ml of EDTA blood was processed on the CellTracks AutoPrep system using CellSearch CEC assay. The enriched cells were stained with nucleic acid dye (DAPI) and anti-CD105 conjugated to phycoerythrin dye (PE) to identify all cells and CECs, respectively. In this example, anti-CD45-FITC was used to label white blood cells. After the staining step, the sample was resuspended in 320 ul of buffer and transferred to a CellSearch analysis cartridge for analysis on the CellTracks Analyzer II. The CellTracks Analyzer II is a 4-color fluorescent microscope which scans in 4 different colors, analyzes images and presents images which are positive in DAPI and CD105-PE. The cells which are positive for DAPI and CD105 and negative for CD45 are counted as CECs. The total numbers of WBCs present in the sample were counted based on DAPI positivity.

For the depletion step, following enrichment and staining, the samples were resuspended in 900 ul of PBS/1% BSA. The samples were then added to the microtiter plate coated with anti-FITC as described in example 4. After one hour, the sample was aspirated and concentrated to 320 ul using a magnetic separator. The sample (320 ul) was then transferred to a cartridge for analysis on CellTracks Analyzer II. The number of CECs and WBCs were determined as described above. The number of CECs and WBCs were compared before and after depletion of WBCs. The results from this study are shown in the Table 4a.

TABLE 4a

Number of CECs and WBCs before and after depletion of WBCs

| Sample # | CECs# Before WBC Depletion | CECs# After WBC Depletion | WBC# Before Depletion | WBC# After Depletion | WBC Depletion (%) |
|---|---|---|---|---|---|
| D587 | 3 | 3 | 11,877 | 1,499 | 87.4 |
| D598 | 2 | 6 | 12,116 | 3,663 | 69.8 |
| D599 | 4 | 4 | 3,463 | Less than 300 | NA |
| D611-1 | 17 | 15 | 12,835 | 2,694 | 79.0 |
| D611-2 | 17 | 12 | 12,427 | 3,307 | 73.4 |
| Ave. | 8.6 | 8 | 10544 | 2791 | 77.4 |

The results clearly show that WBCs can also be removed (>75%) from CECs after enrichment in the CEC assay. In addition, there was no difference in CECs numbers (8.6 vs. 8) before and after depletion. The data indicates that the target cells are not removed even when they are present at very low frequency (<20 cells).

Example 5: Molecular Measurements of WBC Depletion in CellSearch Profile Kit Enriched Samples Duplicate 7.5 ml of EDTA blood from 6 healthy donors was processed on the AutoPrep using a modified CellSeach CTC Profile Kit. The PBS/Biotin reagent in the Profile Kit was supplemented with anti-CD45-FITC at a final reagent concentration of 2 ug/ml so that labeling of WBC takes place on the AutoPrep. Following AutoPrep enrichment, one tube from each donor was subjected to either the "Depleted" protocol which removed the WBC from the sample or the "Non-depleted" protocol which serves as a control to measure the WBC contamination in the sample without the depletion process.

Non-Depleted Protocol

Samples are removed from the AutoPrep and placed in a magnet for 15 minutes. The buffer is aspirated and the cells are Lysed in RLT buffer (Qiagen).

Depleted Protocol

Following AutoPre enrichment, the excess CD45-FITC was removed by washing the sample 2-times with 2 ml of PBS/1% BSA by magnetic separation for 15 minutes. The final sample was resuspended in 900 ul of PBS/5% BSA and then applied to the wells coated with anti-FITC. The samples were incubated for 1 hour with gentle mixing every 15 minutes. After one hour, 300 ul of supernatant was removed from the wells and the cells were placed in a magnet for 15 minutes. The buffer was removed and the cells were lysed in RLT buffer (Qiagen).

For both the depleted and non-depleted samples, the RNA was purified using the Qiagen AllPrep Kit and reverse transcribed using the High Capacity cDNA Reverse Transcription Kits kit (Life Technologies). Complimentary DNA was amplified using TaqMan® PreAmp Master Mix Kit (Life Technologies) and primer sets as for genes from the list in Table 5a. Quantitative PCR was carried out on the amplified samples for two genes known to be expressed in white blood cells (CD45 (aka PTPRC) and BST1) as well as a housekeeping gene expressed (B-Actin). Efficacy of WBC depletion was measured by the loss of WBC and housekeeping specific gene signals in the depleted sample relative to the non-depleted sample.

Figure 4:
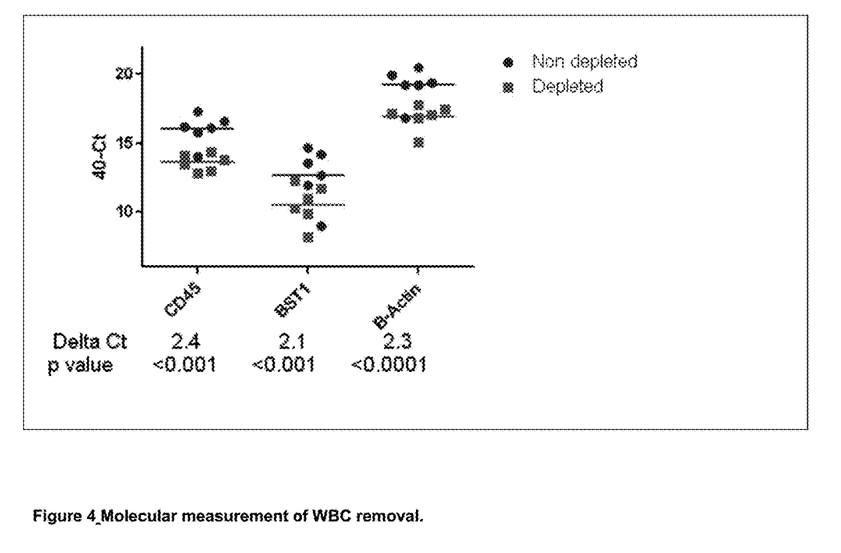
FIG. 4 Molecular measurement of depleted and non-depleted samples
Figure 5:
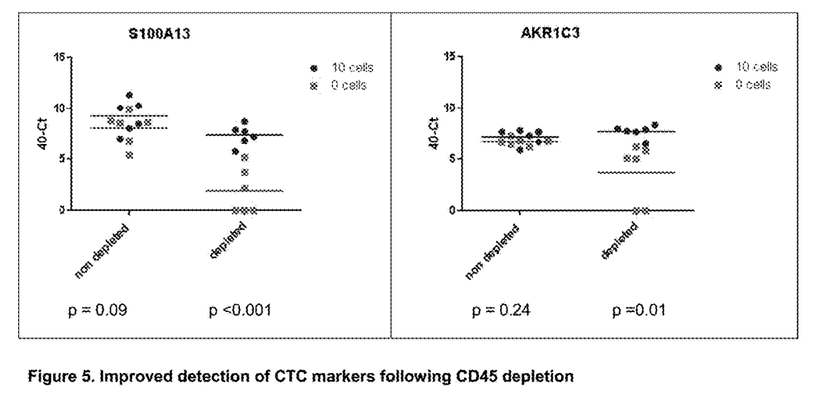
FIG. 5 Detection following CD45 depletion

In FIG. 4 circles and squares represent individual measurements for the on depleted and depleted samples respectively. Lines represent the mean measurement for each sample type. P value represent the results of student's T-tests performed between the depleted and non-depleted samples for each gene measured. T-tests between the depleted and non-deleted samples showed a significant loss of WBC specific and housekeeping genes as a result of CD45 depletion. Mean delta Ct measurements of >2 cycles indicate a >75% reduction of the WBC signals in the CD45 depleted samples.

TABLE 5a

Genes tested with CD45 depletion method:

| Affymetrix Probe Set ID | Gene Symbol | Gene Title |
|---|---|---|
| 205648_at | WNT2 | wingless-type MMTV integration site family member 2 |
| 208711_s_at | CCND1 | cyclin D1 |
| 266_s_at | CD24 | CD24 molecule |
| 201596_x_at | KRT18 | keratin 18 |
| 202589_at | TYMS | thymidylate synthetase |
| 226553_at | TMPRSS2 | transmembrane protease, serine 2 |
| 225330_at | IGF1R | insulin-like growth factor 1 receptor |
| 214352_s_at | KRAS | v-Ki-ras2 Kirsten rat sarcoma viral oncogene homolog |
| 201689_s_at | TPD52 | tumor protein D52 |
| 201005_at | CD9 | CD9 molecule |
| 224559_at | MALAT1 | metastasis associated lung adenocarcinoma transcript 1 (non-protein coding) |
| 218638_s_at | SPON2 | spondin 2, extracellular matrix protein |
| 217776_at | RDH11 | retinol dehydrogenase 11 (all-trans/9-cis/11-cis) |
| 201656_at | ITGA6 | integrin, alpha 6 |
| 209605_at | TST | thiosulfate sulfurtransferase (rhodanese) |
| 204623_at | TFF3 | trefoil factor 3 (intestinal) |
| 202598_at | S100A13 | S100 calcium binding protein A13 |
| 221024_s_at | SLC2A10 | solute carrier family 2 (facilitated glucose transporter), member 10 |
| 226192_at | AR | androgen receptor |
| 212587_s_at | PTPRC | protein tyrosine phosphatase, receptor type, C |
| 205715_at | BST1 | bone marrow stromal cell antigen 1 |
| | TMPRSS2 ERG | T1E4 gene fusion |
| | AKR1C3 | aldo-keto reductase family 1, member C3 (3-alpha hydroxysteroid dehydrogenase, type II) |

Example 6: Improvement of CTC Detection Following White Blood Cell Depletion

One potential advantage of the CD45 depletion method is an improved ability to detect CTC or characterize CTC gene expression when there is some level of background gene expression contributed by the white blood cells. Reducing the number of white blood cells should reduce the background gene expression and improve the ability to detect transcripts in lower numbers of CTC.

To demonstrate this principle four samples were prepared for each of six donors two samples were spiked with 10 VCaP cells and two samples were unspiked. One spiked and unspiked sample was prepared with both the "Depleted" and "Non-depleted" protocol as described in Example 5. RNA extraction, Reverse Transcription and Pre-Amplification kit were carried out as in example 5. Public databases were mined to identify a panel of potential CTC markers that could be useful for measuring utility of the WBC depletion method. Genes were selected that had moderate to high expression in VCaP cells and a range of expression in WBC. RT-PCR results for potential CTC markers S100A13 and AKR1C3. Without WBC depletion (non-depleted samples) both genes show no significant difference in expression between unspiked and 10-cell spiked sample sets. In the depleted set the background contributed by WBC is reduced and there is a significant difference between the unspiked and 10-cell spike sample sets.

Example 7: Application of WBC Depletion for Molecular Characterization of the CTC Following White Blood Cell Depletion The major advantage of the CD45 depletion method is enabling enhanced molecular characterization of the CTC and minimizing the background gene expression contributed by the white blood cells.

Figure 6:
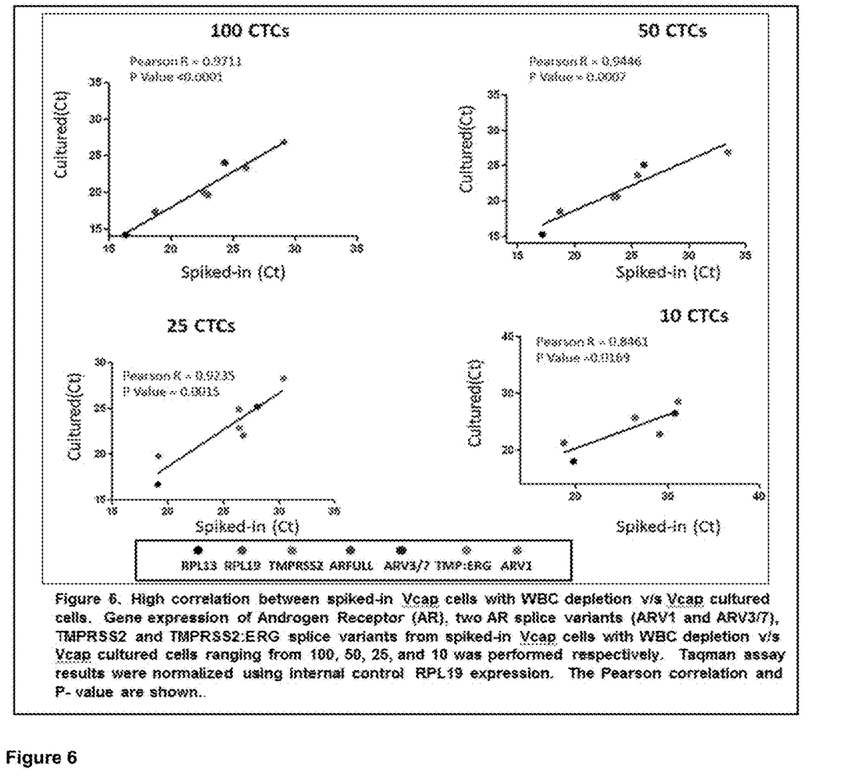
FIG. 6 Correlation between spiked-in Vcap cells with shite blood cell depletion and cultured Vcap cells FIG. 7 Effect of bead depletion.

To demonstrate this application eight samples were prepared from eight donors and two samples each were spiked with 100, 50, 25, and 10 VCaP cells. In addition, four samples containing only VCap cells, for example, 100, 50, 25, and 10 cells were used as positive controls. RNA extraction, Reverse Transcription and Pre-Amplification kit were carried out as in example 6. Androgen Receptor (AR) gene, two AR splice variants (ARV1 and ARV3/7), TMPRSS2 and TMPRSS2:ERG splice variants were selected as the test genes that for VCaP cells. There was a good correlation in the detection of these candidate gene expressions in VCap cells between pure culture VCaP cells and blood spiked with VCap cells after WBC depletion with a correlation coefficient (r2) of >0.9. The results are shown in FIG. 6.

Example 8: Depletion of White Blood Cells Using Bead Based Filtration

This example describes an alternate method for reducing the number of contaminating white blood cells present in samples that have been enriched with the CellSearch Profile Kit. Following EpCAM based immunomagentic enrichment, contaminating CD45+ WBC are labeled with plastic beads. WBC are separated from CTC by passing the mixture through a filter that retains the bead-bound CD45+ cells and passes the unbound CTC. The CTC are then available for molecular or cellular analysis with a reduced number of contaminating WBC.

Figure 7:
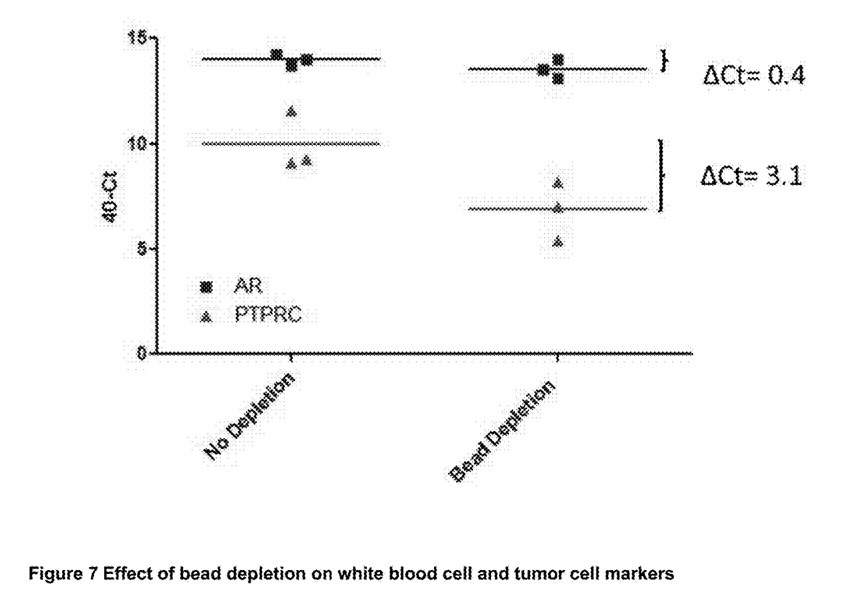

To demonstrate the method 10,000 VCAP cells were spiked into six tubes of healthy donor blood and enriched using the Cell Search Profile kit. Three samples were immediately lysed in Qiagen RLT buffer (non-depleted samples) and the remaining three samples were depleted using the bead based method described below. The enriched fraction containing CTC and contaminating white blood cells were mixed with 30 micron plastic beads that had been coated with an antibody specific for CD45 molecule (pluri-Bead, pluriSelect). The bead/cell mixture was rocked at 8-10 RPM for 1 hour at room temperature. The sample was filtered through a filter with a 27 micron pore size (pluriS-trainer, pluriSelect). The filter was washed 2 times and cells collected in the flow through were analyzed by RT-PCR for a white blood cell specific marker PTPRC (aka CD45) and a tumor cell specific marker androgen receptor (AR). Delta Ct values were created by subtracting the expression level (40-Ct value) of the depleted sample from the expression level of the non-depleted sample. A delta Ct of 3.1 cycles for the white blood cell marker PTPRC indicates that the level of white blood cells has been significantly reduced with the bead depletion protocol relative to a non-depleted sample. A delta CT of only 0.4 cycles for the tumor cell specific marker AR indicates that the bead depletion protocol has little impact on the level of tumor specific markers. The results are shown in FIG. 7, which shows the RT-PCR results for white blood cell and tumor cell markers present in samples that have and have not been subjected to the bead depletion procedure. AR=Androgen Receptor PTPRC=Protein tyrosine phosphatase, receptor type, C.

What is claimed is:

1. A kit for further depletion of white blood cells (WBCs) during enrichment of rare cells comprising: (a) a marker that selectively binds to a rare cell and a white blood cell, wherein the marker is conjugated to a magnetic particle; (b) a leukocyte marker that is conjugated to a hapten; and (c) a solid surface comprising an antibody to the hapten.

2. The kit of claim 1, wherein the rare cell is selected from the group consisting of circulating tumor cells (CTCs), circulating endothelial cells (CECs), circulating multiple myeloma cells (CMMCs), and circulating melanoma cells (CMCs).

3. The kit of claim 1, wherein the marker that selectively binds to the rare cell and the white blood cell is an antibody that binds to an epithelial cell adhesion molecule (EpCAM).

4. The kit of claim 1, wherein the leukocyte marker is an antibody that binds to CD45, CD19, CD15, glycophorin A, CD2, CD14, CD16, CD38, or CD66b.

5. The kit of claim 4, wherein the leukocyte marker is an antibody that binds to CD45.

6. The kit of claim 1, wherein the hapten is selected from the group consisting of fluorescein dye (FITC), phycoerythrin (PE), allophycocyanin (APC) and biotin.

7. The kit of claim 6, wherein the hapten is FITC.

8. The kit of claim 1 further comprising a nucleic acid dye.

9. The kit of claim 8, wherein the nucleic acid dye is 4',6-diamidino-2-phenylindole (DAPI).

10. The kit of claim 1 further comprising an epithelial cell marker.

11. The kit of claim 10, wherein the epithelial cell marker is an anti-cytokeratin antibody.

12. The kit of claim 11, wherein the epithelial cell marker is conjugated to a second hapten.

13. The kit of claim 12, wherein the second hapten is selected from the group consisting of fluorescein dye (FITC), phycoerythrin (PE), allophycocyanin (APC) and biotin.

14. The kit of claim 13, wherein the second hapten is APC.

15. The kit of claim 1 further comprising a rare cell marker, wherein the rare cell marker specifically binds to the rare cell.

16. The kit of claim 15, wherein the rare cell marker is an antibody that binds to CD146 or CD105.

17. The kit of claim 15, wherein the rare cell marker detects a gene selected from any one of S100 calcium binding protein A13 (S100A13) and aldo-keto reductase family 1, member C3 (3-alpha hydroxysteroid dehydrogenase, type II) (AKR1C3).

18. The kit of claim 1, wherein the surface is a microtiter plate or a bead.

* * * * *